(12) United States Patent
Bose et al.

(10) Patent No.: US 8,986,836 B2
(45) Date of Patent: Mar. 24, 2015

(54) MICROSPHERES AND THEIR METHODS OF PREPARATION

(75) Inventors: Anima B. Bose, Athens, OH (US); Junbing Yang, Bolingbrook, IL (US)

(73) Assignee: Ohio University, Athens, OH (US)

( * ) Notice: Subject to any disclaimer, the term of this patent is extended or adjusted under 35 U.S.C. 154(b) by 922 days.

(21) Appl. No.: 12/720,102

(22) Filed: Mar. 9, 2010

(65) Prior Publication Data

US 2010/0237295 A1 Sep. 23, 2010

Related U.S. Application Data

(60) Provisional application No. 61/161,580, filed on Mar. 19, 2009.

(51) Int. Cl.

| | |
|---|---|
| *B32B 5/18* | (2006.01) |
| *H01B 1/04* | (2006.01) |
| *B82Y 30/00* | (2011.01) |
| *C01B 3/00* | (2006.01) |
| *C01B 31/02* | (2006.01) |
| *C01B 31/10* | (2006.01) |
| *A61M 1/36* | (2006.01) |

(52) U.S. Cl.
CPC . *H01B 1/04* (2013.01); *B82Y 30/00* (2013.01); *C01B 3/0021* (2013.01); *C01B 3/0084* (2013.01); *C01B 31/02* (2013.01); *C01B 31/10* (2013.01); *A61M 1/3679* (2013.01); *Y02E 60/325* (2013.01); *Y10S 977/773* (2013.01); *Y10S 977/775* (2013.01); *Y10S 977/932* (2013.01); *Y10S 977/948* (2013.01); *Y10S 977/962* (2013.01)
USPC ... 428/402; 252/502; 252/518.1; 252/519.14; 428/402.24; 502/180; 502/202; 977/773; 977/775; 977/932; 977/948; 977/962

(58) Field of Classification Search
USPC ............. 252/500–518.1, 519.14; 428/402, 428/402.24; 502/180, 202; 977/773, 775, 977/932, 948, 962
See application file for complete search history.

(56) References Cited

U.S. PATENT DOCUMENTS

| | | | |
|---|---|---|---|
| 4,171,283 A | 10/1979 | Nakashima et al. | |
| 5,908,896 A | 6/1999 | Mayer et al. | |
| 6,294,501 B1 * | 9/2001 | Chang | 502/418 |
| 6,692,718 B1 * | 2/2004 | Osawa | 423/448 |
| 6,716,525 B1 | 4/2004 | Yadav et al. | |

(Continued)

FOREIGN PATENT DOCUMENTS

| | | | | |
|---|---|---|---|---|
| CN | 1557702 A | * | 12/2004 | ............. C01B 31/02 |
| GB | wo2007020410 A1 | * | 2/2007 | ............. G01N 33/00 |

(Continued)

OTHER PUBLICATIONS

Cermignani ("Synthesis and Characterization of Boron-Doped Carbons." Carbon, 33(4), pp. 367-374, pub 1995).*

(Continued)

*Primary Examiner* — Tri V Nguyen
(74) *Attorney, Agent, or Firm* — Wood, Herron & Evans, LLP

(57) ABSTRACT

Carbon microspheres are doped with boron to enhance the electrical and physical properties of the microspheres. The boron-doped carbon microspheres are formed by a CVD process in which a catalyst, carbon source and boron source are evaporated, heated and deposited onto an inert substrate.

7 Claims, 2 Drawing Sheets

(56) References Cited

U.S. PATENT DOCUMENTS

| | | | |
|---|---|---|---|
| 2004/0035751 A1* | 2/2004 | Plee | 208/113 |
| 2004/0110005 A1* | 6/2004 | Choi et al. | 428/402 |
| 2004/0132220 A1 | 7/2004 | Fish | |
| 2005/0025970 A1 | 2/2005 | Stipanovic | |
| 2006/0008404 A1* | 1/2006 | Hwang | 423/445 B |
| 2006/0137487 A1* | 6/2006 | McKinnon et al. | 75/252 |
| 2007/0183959 A1 | 8/2007 | Charlier et al. | |
| 2008/0011617 A1* | 1/2008 | Struthers et al. | 206/0.7 |
| 2008/0119576 A1 | 5/2008 | Young et al. | |
| 2008/0185560 A1* | 8/2008 | Roach | 252/503 |
| 2008/0266754 A1* | 10/2008 | Kazaryan et al. | 361/508 |
| 2009/0060832 A1* | 3/2009 | Zhou et al. | 423/658.2 |
| 2009/0123789 A1* | 5/2009 | Cooper et al. | 429/13 |
| 2009/0294273 A1 | 12/2009 | Monsen et al. | |

FOREIGN PATENT DOCUMENTS

| | | | | |
|---|---|---|---|---|
| JP | 2008050237 | * | 3/2008 | C01B 31/08 |
| WO | 2005122285 A2 | | 12/2005 | |

OTHER PUBLICATIONS

Mondal ("Boron-doped carbon microspheres." Mater. Chem. and Phys., 114, pp. 973-977, 2009).*

Konno et al. ("Formation and characterization of carbon microspheres doped with boron and nitrogen." Tanso, 219, p. 221-225, pub 2005).*

Perez-Cadenas et al. ("Surface Chemistry, Porous Texture, and Morphology of N-DopedCarbon Xerogels." Langmuir, 25, pp. 466-470, pub online Dec 9, 2008).*

Burgess et al. ("Boron-doped carbon powders formed at 100 0C and one atmosphere." Carbon, 46, pp. 1711-1717, pub online Jul. 2008).*

Jacques et al. ("LPCVD and Characterization of Boroncontaining Pyrocarbon Materials." Carbon, 34(9), pp. 1135-1143, pub 1996).*

Kim et al. ("Nondissociative Adsorption of H2 Molecules in Light-Element-Doped Fullerenes" Phys Rev Let, 96(1), p. 016102-1 to 4, Jan. 13, 2006).*

Terres et al. ("Hydrogen storage in spherical nanoporous carbons." Chem Phys Let, 403, pp. 363-366, 2005).*

Cabria et al. ("The optimum average nanopore size for hydrogen storage in carbon nanoporous materials." Carbon, 45, pp. 2649-2658, Aug. 2007).*

International Search Report and Written Opinion mailed Jul. 6, 2010.

Kouvetakis, Kaner, Sattler, Bartlett, A novel graphite-like material of composition BC3, and nitrogen-carbon graphites, J. Chem. Doc. Cjhem. Commun. 1986, pp. 1758-1759.

Chesneau, Beguin, Conard, Erre, Thebault, The antioxidation effect of boron oxide on a pyrocarbon, J. Carbon, 1992, 30, pp. 714-716.

Ma, Wang, Chen, Cermignani, Schobert, Patano, Semi-empirical studies on electronic structures of a boron-doped graphene layer—Implications on the oxidation mechanism, Carbon, 1997, vol. 35, No. 10-11, pp. 1517-1525.

Lowell, Solid solution of boron in graphite, J. Am Ceram Soc., 1967, 50(3), pp. 142-144.

Wagner, Dickinson, Ambient and high temperature experiments on boron-doped polycrystalline graphites, Carbon, 1970, vol. 8, pp. 313-320.

Jones, Thrower, Influence of boron on carbon fiber microstructure, physical properties, and oxidation behavior, Carbon, 1991, vol. 29, No. 2, pp. 251-269.

Zhong, Sano, Uchiyama, Kobayashi, Effect of low-level boron doping on oxidation behavior of phlyimide-derived carbon films, Carbon, 2000, 38, pp. 1199-1206.

Stephan, Ajayan, Colliex, Redlich, Lambert, Bernier, Lefin, Doping graphitic and carbon nanotube structures with boron and nitrogen, Science, 1994, vol. 266, No. 5191, pp. 1683-1685.

M. Terrones, N. Grobert, H. Terrones, Synthetic routes to nanoscale BxCyNz architectures, Carbon, 2002, 40, pp. 1665-1684.

Yang, Ling, Liu, Kang, Huang, Wu, Preparation and properties of phenolic resin-based activated carbon spheres with controlled pore size distribution, Carbon, 2002, 40, pp. 911-916.

Hupert, Much, Wang, Stotter, Cvackova, Haymond, Show, Swain, Conductive diamond thin-films in electrochemistry, Diamond and Related Materials, 2003, 12, pp. 1940-1949.

Paik, Jarvi, Grady, Extent of PEMFC cathode surface oxidation by oxygen and water measured by CV, Electrochem. Solid-State Lett., 2004, 7, A82-A84.

Kangasniemi, Condit, Jarvi, Characterization of vulcan electrochemically oxidized under simulated PEM fuel cell conditions, J. Electrochem. Soc., 2004, 151, E125-E132.

Acharya, Turner, Stabilization of platinum clusters by substitutional boron dopants in carbon supports, J. Phys. Chem B (letters), 2006, 110, pp. 17706-17710.

D.L. Wilcox, Sr. and M Berg, Microsphere Fabrication and Applications: An Overview, Mat. Res. Soc. Symp. Proc. vol. 372, 1995, pp. 3-13.

Hepatic Assist System Using Bead-Type Charcoal, I. Amano, H. Kano, H. Takahira, Y. Yamamoto, K. Itoh, S. Iwatsuki, K. Maeda, and K. Ohta, et al., editors, Artificial Liver and Artificial Cell, New York: Plenum Press, 1978, pp. 89-98.

* cited by examiner

MICROSPHERES AND THEIR METHODS OF PREPARATION

RELATED APPLICATION

This application is related to and claims the benefit of U.S. Provisional Patent Application Ser. No. 61/161,580, filed Mar. 19, 2009, the disclosure of which is incorporated herein by reference.

GOVERNMENT RIGHTS

This invention was made with Government support under Contract No. DE-AC02-06CH11357, awarded by the US Department of Energy, and Contract IL-26-7006-01 05P 08-282 awarded by the Department of Transportation. The Government has certain rights in this invention.

BACKGROUND OF THE INVENTION

Carbon microspheres, which generally have a particle size less than about 700 nanometers, have a wide variety of potential applications. These microspheres can be used as catalyst supports, as a medium for storing hydrogen, and as adsorbants, such as in the case of hemoperfusion and ultrafiltration membranes. These microspheres are nanoporous particles which are prepared by chemical vapor deposition. However, their use is somewhat limited by a lack of activity, in particular, electrical conductivity.

SUMMARY OF THE INVENTION

The present invention is premised on the realization that boron-doped carbon microspheres can be prepared, and can be used in a wide variety of applications including nano wiring and integrated circuits, and have superior physical properties relative to carbon microspheres.

The objects and advantages of the present invention will be further appreciated in light of the following detailed description and drawing in which:

DETAILED DESCRIPTION

Figure 1:
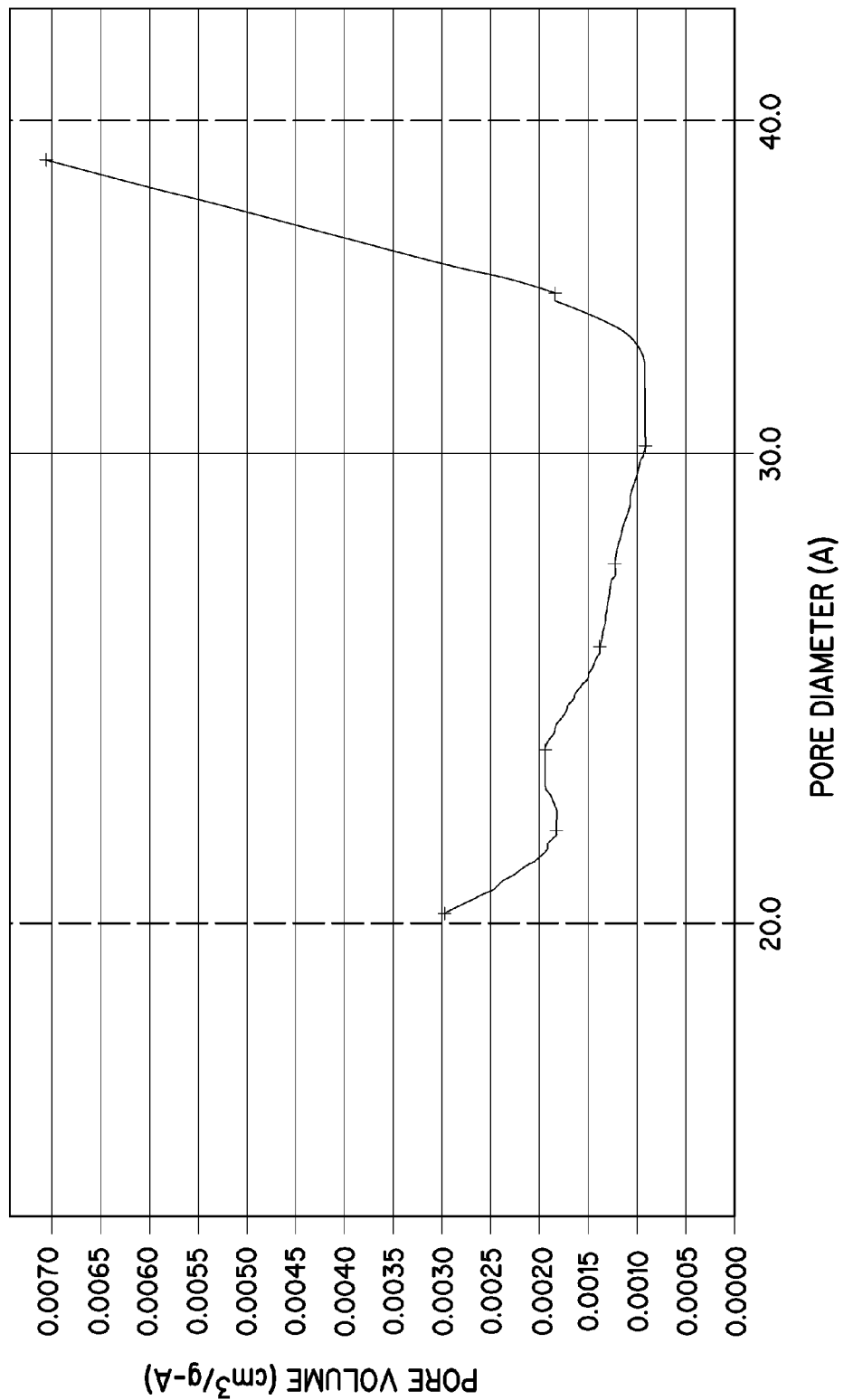
FIG. 1 is a graph of the BJH desorption differential pore volume distribution of boron-doped carbon microspheres (BCMS).

The boron-doped carbon microspheres of the present invention are microspheres having a diameter of less than about 700 nm and generally less than 500 nm, or less than 100 nm down to about 50 nm. The microspheres are further considered to be nanoporous wherein the spheres include pores having a diameter generally in the range of 0.6 nm to about 2 nm These microspheres are formed from a combination of carbon and boron. The major component of the microspheres is carbon. The boron-doped carbon microspheres of the present invention are formed by chemical vapor deposition. In the chemical vapor deposition process, the reactants are injected into a flowing gas stream and are vaporized. The flowing gas stream, including the reactants, is heated further and impacted against a substrate and the carbon microspheres deposit on the substrate.

The reactants include a carbon source gas, a boron source, as well as a catalyst. Generally, any typical catalyst suitable for use in forming carbon microspheres can be employed. Iron, nickel and cobalt catalysts can be used. One typical catalyst is ferrocene.

The carbon source can be any hydrocarbon, either saturated or unsaturated and may be aromatic. In particular, compounds such as benzene and xylene are particularly suitable for use in the present invention as a carbon source.

The boron source must be a compound that can be formed into a vapor at reaction temperatures without decomposing. Generally, a vapor is formed by dissolving a boron containing compound into an appropriate solvent, preferably a hydrocarbon solvent, and then injecting this into the chemical vapor deposition reactor. As is described below, it is convenient to dissolve the boron source into the carbon source.

Suitable boron containing compounds include the halides, such as boron triflouride and boron trichloride, as well as other compounds that can be dissolved in an appropriate solvent such as nitrates, and the like. Generally, the stoichiometric ratio of boron to carbon will be 1 to 20 to 1.5 to 10 generally 1 to 9 to 1 to 10.

The reaction is conducted in a chemical vapor deposition reactor with a suitable deposition substrate. The deposition substrate must be inert under reaction conditions. Suitable substrates include magnesium oxide, aluminum oxide, indium tin oxide, as well as quartz.

Chemical vapor deposition reactors include a heating zone and a reaction zone. To form the microspheres, the heating zone is maintained at a temperature sufficient to vaporize the reactants, typically about 200° C. The reaction zone is maintained at a much higher temperature, generally above 650° C. for this reaction, typically about 850-1000° C. The reaction is conducted by forming a solution of the reactants, including the catalyst, carbon source and boron source, in the desired stoichiometric relation. This is injected into the heating zone into a flowing gas stream.

The flowing gas stream can be a variety of inert gases, but typically are nitrogen or argon, or mixtures thereof. Hydrogen may also be included to avoid soot formation, if needed. Further, a nitrogen source gas such as ammonia may be added to facilitate boron inclusion into the microspheres.

If ammonia is added, it will generally comprise about 10% of the partial pressure of the gas stream. Hydrogen will comprise 0-20% of the partial pressure of the gas stream. Generally, the ratio of ammonia to hydrogen to inert gas (Ar) will vary from 1:1:1: to 1:4:4 by volume. The flowing gas stream draws the reactants from the heating zone where they are vaporized into the reaction zone where they form the boron-doped carbon microspheres on the selected substrate, typically quartz.

When the nitrogen source gas, ammonia, is added, it is believed that the nitrogen bonds to carbon and bonds to the boron. If ammonia is not present, the boron bonds directly to the carbon. This latter reaction is not as thermodynamically favored as the nitrogen carbide formation. Thus, the addition of ammonia increases the incorporation of boron into the microspheres.

Typically, the reactor is purged with an inert gas to remove all oxygen from the system prior to the reaction. After purging, the flow of gas is started. The reactants are then introduced in the desired ratio into the flowing gas stream. After an appropriate period of time, generally 5 minutes to 1 hour, the injection of the reactants is discontinued and the furnace cooled down to room temperature under argon and hydrogen.

The formed microspheres can be subjected to a mild oxidation in order to open the porous structure. In order to do so, the preheating zone is heated to a temperature of about 500° C., and the reaction zone to about 850° C. Deionized water is simply injected into the preheating zone and evaporated and transported into the reaction zone in flowing argon. This is continued again for about 30 minutes. The furnace is then cooled down to room temperature under flowing argon.

The invention will be further appreciated in light of the following detailed examples.

EXAMPLE 1

Synthesis of BCMS

Boron-doped carbon microspheres (BCMS) were prepared by a chemical vapor deposition process inside a quartz tube inserted through a low-temperature heating section (Zone I, 200° C.) and a high-temperature heating section (Zone II, 950° C.).

0.34 g Ferrocene was dissolved in 23.63 g boron trichloride solution 1.0 M in p-xylene (both from Sigma-Aldrich) and used as precursor for BCMS synthesis. The solution was injected and vaporized in Zone I. A hydrogen and argon mixture (60 ml/min and 90 ml/min, respectively) was used to transport the vapor from Zone I to Zone II. The BCMS were formed over a polished quartz plate inside Zone II. After 30 minutes, the solution injection was stopped and the furnaces were cooled down to room temperature with the argon and hydrogen flowing.

EXAMPLE 2

Activation of BCMS

The boron-doped carbon microspheres (BCMS) formed in Example 1 were activated in steam to open the pore structure. For this purpose, Zone I and Zone II were heated and kept at 500° C. and 850° C., respectively. Deionized water was injected into and evaporated inside the quartz tube in the middle of Zone I at the rate of 0.225 ml/min. Flowing argon (140 ml/min) was used to carry the steam to Zone II and react with BCMS, which were synthesized as disclosed in Example 1. The injection of water lasted for 30 minutes. After stopping the injection of water and turning off the temperature controller, the furnace was cooled down to room temperature with flowing argon.

The boron-doped carbon microspheres formed from the above examples were spherical particles with uniform particle size. TEM images reveal that the microspheres have an onion structure, and x-ray photon electron spectrum indicated they are comprised of carbon, boron and oxygen an impurity. Generally, the boron to carbon ratio is approximately from 1:4-1:12.

The microspheres are high purity uniform spheres of about 700 nanometers or less in diameter, and reasonably high surface area of about 220 $m^2/g$ measured via nitrogen absorption.

Further, thermogravimetric analysis demonstrates that the oxidation stability is comparable to pure multiwall nanotubes. The activated microspheres contain a large number of mesopores and the BET surface area is about 213 $m^2/g$, which is the same range as standard carbon black, but higher than multiwall carbon nanotubes. The sheet resistance of the microspheres is lower than that formed from multiwalled carbon nanotubes. The micropore surface area was 107 $m^2/g$ and the total pore volume was 0.163 $cm^3/g$. The micropore volume was 0.054 $cm^3/g$ and the median micropore diameter was 0.62 nm. FIG. 1 shows the pore size distribution of the activated mircospheres. The activated microspheres clearly contain a large number of mesospheres.

EXAMPLE 3

Incorporation of Nitrogen 0.5 g Ferrocene was dissolved in 28.0 g boron trichloride solution in 1.0 M p-xylene (both from Sigma-Aldrich) and used as precursor for BCMS synthesis. The solution was injected into the same reactor as in Example 1 and fully vaporized in the low-temperature zone I (200° C.). A carrier gas mixture containing ammonia, hydrogen and argon with pre-set volume ratio (volume ratio $NH_3/H_2/Ar=1/1.33/4$ and total flow rate of 190 ml/min) was added through upstream of zone I. BCMS formed on the surface of a quartz substrate positioned in the high-temperature zone at 900° C. The growth process lasted for 30 minutes until the liquid precursor injection stopped. The carrier gas continued to flow for another 20 minutes before the reactor was cooled down.

The boron-doped carbon microspheres of the present invention can be used in a variety of different applications. In particular, these can be used in fuel cells, which are devices that convert chemical energy of fuels, such as hydrogen, directly into electrical energy. The proton exchange membrane fuel cell is one type of fuel cell that can utilize the boron-doped carbon microspheres of the present invention. The boron-doped carbon microspheres can be used in any fuel cell operating at less than 500° C. These can be combined with an electron conducting resin or used on other supports.

Also, the boron-doped carbon microspheres of the present invention can provide a durable catalyst support. The uniform pore size of the microspheres allow the microspheres to carry gases through their porous structure. In particular, the unique spherical structure and high thermal stability and oxidation resistance of the boron-doped carbon microspheres compared to carbon black, carbon fibers or carbon nanotubes, enable this product to be used as a catalyst support in which its uniform rate of gas transport does not degrade. Thus, the microspheres can be used as supports for electrolytic cell cathodes or anodes. These would be used in the electrolysis of water, ammonia or dissolved organic material.

Figure 2:
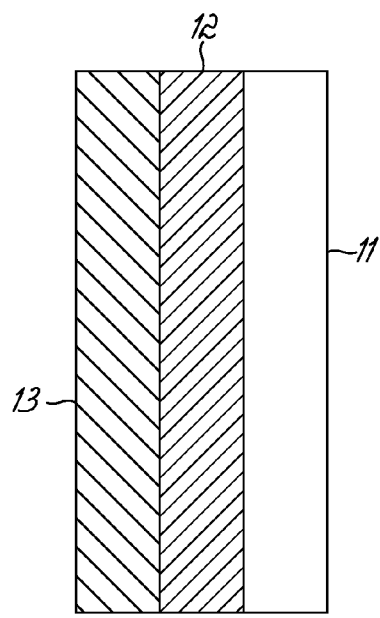
FIG. 2 is a diagrammatic depiction of a catalyst support.
Figure 3:
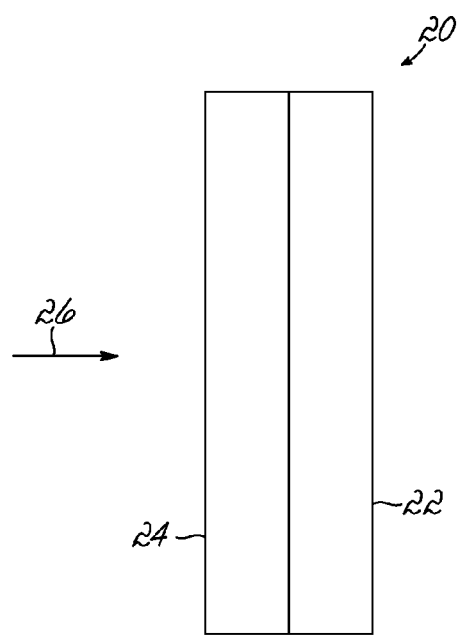
FIG. 3 is a diagrammatic depiction of a hemoperfusion filter.

The catalyst support can take the configuration shown in FIG. 2 in which a porous conductive support layer 11 is coated with a layer 12 of the boron-doped carbon nanospheres. This layer is in turn coated with a catalyst 13 such as a noble metal. The catalyst can be deposited by well known methods such as vapor deposition, electrochemical deposition and chemical deposition. Exemplary catalysts include platinum, iridium, ruthenium, rhenium, palladium, gold, silver, nickel, iron, lanthanides and alloys of these. Basically, any catalyst can be supported by these microspheres, including nonmetallic catalysts as well as metallic catalysts.

The boron-doped carbon microspheres of the present invention can also be used as an adsorbant to store gases such as hydrogen. In this application, hydrogen is typically stored under elevated pressure, and frequently at reduced temperatures, causing the hydrogen to migrate into the boron-doped carbon microspheres. The boron, in particular, enhances the hydrogen absorption via a non-classical chemical binding mechanism in which the two undissociated H atoms in the molecule and the B form a 3-body center sharing two common electrons. Further the high surface area increase $H_2$ absorption.

Also, due to the ability of the microspheres to absorb organic compounds, the microspheres of the present invention can be used as a drug delivery system, absorbing pharmacologically active organic compounds, and gradually releasing them subsequent to administration.

In another application, the boron-doped carbon microspheres of the present invention can be used as adsorbants in a wide variety of different applications, and, in particular, in hemoperfusion applications. The uniform size of these spheres, along with their porous structure, both facilitate in use in hemoperfusion in place of activated carbon.

As shown in FIG. 2, the hemoperfusion filter 20 would include a porous support layer 22 coated with a layer of the boron-doped carbon microspheres 24. Blood or other fluid would flow through the filter 20 in the direction of arrow 26. Organic molecules will tend to bond to the microspheres thereby filtering the fluid.

The boron-doped carbon microspheres possess a much higher electrical conductivity than carbon nanotubes while being stable at higher temperatures. For that reason, the microspheres can be used in a variety of different applications.

These microspheres are particularly useful in batteries as a conductive surface and/or support. The microspheres can form conductive surfaces in metal ion batteries as well as metal hydride batteries and other batteries such as metal/air batteries. These microspheres can also replace carbon in the cathodes and anodes in batteries, fuel cells and electrolytic cells. They can also comprise nonometer size conductors or nano wiring for micro circuits.

The boron-doped carbon microspheres can be used in any application requiring electrical conductivity, and, in particular can be used to replace indium tin oxide in a variety of different applications, including solar panels, and the like. In particular, the boron-doped carbon microspheres can be added to photoactive compositions and used to form thin layer solar panels.

Thus, the boron-doped carbon microspheres of the present invention can be used in a wide variety of different applications because of their enhanced support stability through boron doping, enhanced catalyst support interaction providing improved stability, high electronic conductivity, spherical particle shape permitting uniform packing density.

This has been a description of the present invention along with the preferred method of practicing the present invention. However, the invention itself should only be defined by the appended claims.

Wherein we claim:

1. Carbon microspheres having an average diameter of 50 to 700 nm wherein microspheres are doped with boron;
    said sphere having pores wherein said pores are 0.6 to 2 nanometers;
    wherein a gas is stored in said microsphere.
2. The carbon microspheres claimed in claim 1 wherein the boron to carbon ratio of said microspheres is at least 1:20.
3. The carbon microspheres claimed in claim 2 wherein the boron to carbon ratio of said carbon microspheres is less than 1.5 to 10.
4. The carbon microspheres claimed in claim 3 wherein the boron to carbon ratio of said microspheres is from about 1:4-1:12.
5. The carbon microspheres claimed in claim 1 further comprising nitrogen.
6. The microspheres claimed in claim 1 wherein said gas is $H_2$.
7. A separator for an electrolytic cell comprising a support containing the carbon microspheres claimed in claim 1.

* * * * *